United States Patent [19]
Huang et al.

[11] Patent Number: 6,121,247
[45] Date of Patent: *Sep. 19, 2000

[54] THERAPY FOR ALLERGIC DISEASES

[75] Inventors: Shau-Ku Huang, Towson; Marsha Wills-Karp, Laurel; Xiu-Min Li, Baltimore, all of Md.; Andrea Keane-Myers, Brookline, Mass.

[73] Assignee: The Johns Hopkins University, Baltimore, Md.

[*] Notice: This patent issued on a continued prosecution application filed under 37 CFR 1.53(d), and is subject to the twenty year patent term provisions of 35 U.S.C. 154(a)(2).

[21] Appl. No.: 08/826,050

[22] Filed: Mar. 28, 1997

[51] Int. Cl.$^7$ .............................. A61K 48/00; C12N 15/00
[52] U.S. Cl. ............................................ 514/44; 435/320.1
[58] Field of Search .................................... 424/449; 514/1, 514/2, 26, 169, 183, 153, 556, 44; 604/20; 435/320.1

[56] References Cited

U.S. PATENT DOCUMENTS

| | | | |
|---|---|---|---|
| 5,641,662 | 6/1997 | Debes et al. | 435/172.1 |
| 5,709,853 | 1/1998 | Iino et al. | 424/85.6 |

OTHER PUBLICATIONS

McCray et al. (1995) J. Clin. Invest., vol. 95, 2620–2632, Jun. 1995.

Yet et al. (1994) Gene Therapy, vol. 1 192–200, 1994.

Verma et al. (1997) Nature, vol. 389, 239–242, Sep. 1997.

Rudikoff et al. (1998) The Lancet, vol. 351, 1715–1721, Jun. 1998.

Orkin et al. (1995) "Report and Recommendations of the Panel to Assess the NIH / Investment in Research on Gene Therapy", 1995.

Jolly D. (Cancer Gene Therapy, vol. 1, No. 1, 1994, pp. 51–64).

Santing et al. (European J. Pharmacology, (Mar. 11, 1994) 254 (1–2) 49–57) Abstract only.

Mapp et al. (American Review of Respiratory Disease, (1985 Aug)132 (2) 292–8 Abstract only.

Marsh et al. American Review of Respiratory Disease, (1985 Jun.) 131 (6) 875–9) Abstract only.

Johnson et al. (Agents and Actions, (1986 Jun.) 18 (3–4) 301–5) Abstract only.

NIH panel report, Dec. 1995.

Robbins et al. Pathological basis of disease, 1984, p. 727.

*Primary Examiner*—Scott D. Priebe
*Assistant Examiner*—Anne Marie S. Beckerleg
*Attorney, Agent, or Firm*—Banner & Witcoff, Ltd.

[57] ABSTRACT

Administration of an expression gene construct for IFN-γ to an affected organ is an effective means of reversing antigen-induced inflammation. Suitable allergic diseases for treatment include atopic asthma, rhinitis, and dermatitis.

8 Claims, 8 Drawing Sheets

SEQUENCE LISTING

<160> NUMBER OF SEQ ID NOS: 5

<210> SEQ ID NO 1
<211> LENGTH: 24
<212> TYPE: DNA
<213> ORGANISM: Mouse

```
<400> SEQUENCE: 1
tcagcagcga ctccttttcc gctt                                              24

<210> SEQ ID NO 2
<211> LENGTH: 25
<212> TYPE: DNA
<213> ORGANISM: Mouse

<400> SEQUENCE: 2
gttggataca ggccagactt tgttg                                             25

<210> SEQ ID NO 3
<211> LENGTH: 25
<212> TYPE: DNA
<213> ORGANISM: Mouse

<400> SEQUENCE: 3
gattcaactt gcgctcatct taggc                                             25

<210> SEQ ID NO 4
<211> LENGTH: 25
<212> TYPE: DNA
<213> ORGANISM: Mouse

<400> SEQUENCE: 4
tcagaagaac tcgtcaagaa ggcga                                             25

<210> SEQ ID NO 5
<211> LENGTH: 24
<212> TYPE: DNA
<213> ORGANISM: Mouse

<400> SEQUENCE: 5
atgaacgcta cacacactgc atct                                              24
```

THERAPY FOR ALLERGIC DISEASES

This application claims the benefit of provisional application Ser. No. 60/014,398 filed on Mar. 29, 1996.

This invention was made using funds from the U.S. National Institutes of Health, Grant No. AI34002. Therefore, the government retains certain rights in the invention.

BACKGROUND OF THE INVENTION

Allergic diseases are of great public health concern as more than 20% of the U.S. population alone are afflicted with these chronic and often debilitating diseases. In particular, despite increased usage of medications, deaths from asthma have risen by 72%. These findings highlight the need for improved therapeutic strategies.

Allergic diseases (including allergic rhinitis, allergic dermatitis, and allergic asthma) are characterized by tissue inflammatory responses. Numerous clinical and experimental animal studies have indicated a pivotal role of cytokines in the development of allergic inflammatory responses. In particular, a subset (Th2) of CD4$^+$ T cells, which has been distinguished functionally by its pattern of cytokine secretion, is thought to play a key role. Th2 cells are thought to promote allergic responses through their secretion of the cytokines, IL-4 and IL-5, which promote IgE production and mast cell development, and eosinophilia, respectively. Cytokines released by the opposing pathway (Th1), such as IFN-γ, inhibit the development and expansion of Th2 cells and cytokine production.

Airway hyperreactivity seen in asthma is associated with an inflammatory response characterized by the presence of eosinophils and activated $T_{H2}$-lymphocytes infiltrating the bronchial mucosa (8, 9, 10, 11, 13, 15, 16). However, the sequence of events leading to inflammatory responses and bronchial hyperreactivity are still unclear. The precise regulatory role of T cells and cytokines involved in the inflammatory responses are as yet to be determined.

It has been previously suggested that IFN-γ may prove beneficial in the treatment of allergic responses in mice (9, 16, 20). In a pilot study to evaluate the effects of nebulized recombinant IFN-γ protein in patients with mild atopic asthma, Boguniewicz et al. (2) demonstrated that four of five patients had a decrease in the percent of eosinophils, however, no improvement in pulmonary function was observed in any patient. In addition, they showed that there was no significant decrease in airway inflammation associated with nebulized IFN-γ. Previous studies in murine models of allergy have demonstrated that short term systemic delivery of IFN-γ did not provide sufficiently high levels of IFN-γ in the lungs, and consequently was not effective in reversing antigen-induced allergic responses (16). In addition, recombinant IFN-γ given systemically has severe side effects, such as fever, impaired function of the kidneys, and heart, leucocytopenia, and considerable loss of weight. However, short term nebulization of IFN-γ to normal human airways did not induce such effects. Injected cytokine proteins are often short-lived and dissipate quickly in vivo, which limits their potential in vivo therapeutic use. Moreover, repeated injections are required to reach therapeutic efficacy. Thus there is a need in the art for new methods for delivering cytokines to the critical portions of the body for treatment of antigen-induced allergies.

SUMMARY OF THE INVENTION

It is an object of the invention to provide methods for treating atopic diseases.

This and other objects of the invention are provided by one or more of the embodiments described below. In one embodiment of the invention a method for treating atopic diseases is provided. The method comprises the step of: locally administering to a patient who has an atopic disease a preparation comprising a DNA expression construct comprising a human IFN-γ coding sequence, whereby one or more symptoms of the atopic disease of the patient is alleviated.

The present invention thus provides the art with a therapeutic method for treating an increasingly important health problem.

BRIEF DESCRIPTION OF THE DRAWINGS

FIG. 1. Generation of a murine IFN-γ gene expression construct. The IFNγ- gene coding region was amplified from Con A-stimulated mouse spleen cells by PCR. The PCR products were cloned in a "TA" vector and an Xho I-XhoI fragment of the insert was further cloned into the polylinker site of an expression vector, pcDNA3 (Invitrogen). This shuttle vector contains a CMV promoter, bovine growth hormone poly A tail, and a neo gene to allow in vitro selection. The expression of neo gene is driven by a SV40 early promoter. The orientation and sequence of the IFN-γ insert was confirmed by sequencing. The plasmid DNAs were propagated in *E. coli* (JM103) and purified by cesium chloride gradient purification to ensure the purity and to minimize endotoxin contamination.

FIG. 2. Production of IFN-γ in transduced epithelial cells. The IFN-γ transgene in a plasmid/LipofectAmine complex was delivered in vitro to epithelial cells of the human epithelial cell line, BEAS-2B, in the log phase of growth. Forty-eight hours post-transfection, neomycin-resistant cells were selected and the supernatants were collected and assayed for IFN-γ by ELISA.

FIGS. 3. (A–B) Detection of transduced IFN-γ genes in vivo. Lung sections of mice were preheated with 10 µg/ml proteinase K at 37° C. for 7 min. Hybridizations were performed by using sense- and antisense-IFN-γ riboprobes labeled with digoxigenin. Hybridization of pcDNA (vector)- and pcDNAIFN-treated lung tissues were performed in parallel overnight, followed by the treatment with anti-digoxigenin Ab conjugate for one hr at RT. Following extensive washings, the slides were treated with color substrate containing NBT and X-phosphate. The slides were then counter-stained with Nuclear Fast Red, and mounted. Representative results of pcDNA-(mock; FIG. 3A) and pcDNAIFN-treated (FIG. 3B) lungs (distal bronchiols) at 24-hr time point are shown.

FIGS. 5. (A–D) Airway reactivity to i.v. acetylcholine. (FIGS. 5A and 5C) Male AKR and A/j mice (6–8 weeks old; 6–8 mice per experimental group) were sensitized i.p. with conalbumin (CA; 100 µg in 400 µl volume) or PBS 14 days prior to intratracheal challenges with either PBS or CA (50 µg). Three days prior to intratracheal challenge, mice aspirated 50 µl of the following: PBS alone, lipofectamine alone (15 µl lipofectamine in a total volume of 50 µl PBS); pcDNA+lipofectamine (5 µg plasmid+15 µl of lipofectamine); or pcDNAIFN+lipofectamine (5 μg plasmid+15 μl of lipofectamine). Three days after the challenge, BALs were collected for cell differentials and (FIGS. 5B and 5D) airway reactivity to acetylcholine was examined.

FIGS. 6. (A+B) Airway reactivity to i.v. acetylcholine In AKR mice adoptively transferred by a conalbumin-specific Th2 clone.

An Ag-specific T-cell clone, D10.G4.1 (D10; purchased from ATCC, Rockville, Md.) is a conalbumin (CA)-specific $T_{H2}$ clone drived from AKR/J mice (7). D10 cells were stimulated periodically with CA (100 μg/ml) in the presence of irradiated AKR spleen cells as APCs. Prior to cell transfer, D10 cells were kept in culture for 8 days after stimulation, and the viable cells were isolated and suspended in media containing Ag (CA, 4 mg/ml) or an irrelevant Ag, (RW, 4 mg/ml) or PBS. In addition, the spleen cells from naive AKR mice were transferred into mice for comparison. The cell suspension ($5 \times 10^6$ cells in 0.05 ml) from various conditions was transferred intratracheally into the mouse lungs. Control mice received either Ag alone, or PBS, or remained untreated. At various time points after cell transfer, airway responsiveness (FIG. 6B), and the BAL cell differential counts (FIG. 6A) were determined as described above. Differences in the inflammatory cell numbers, airway responsiveness among groups of mice were determined using analysis of variance (StatView). When differences among groups are significant ($p < 0.05$), Fisher's protected least significant difference test were used to distinguish between pairs of groups.

FIGS. 7. (A+B) In vivo efficacy of mucosal IFN-γ gene transfer in Th2 cell-adoptively transferred mice (FIG. 7A) Naive male AKR mice (6 weeks old; 4 mice per group) were used following the same protocol as described in the legend to FIG. 6. Forty-eight or 72-hr prior to the cell transfer, mice aspirated 50 μl of the following: PBS alone, lipofectamine alone (15 μl lipofectamine in a total volume of 50 μl PBS); pcDNA +lipofectamine (5 μg plasmid+15 μl of lipofectamine); or pcDNAIFN+lipofectamine (5 μg plasmid+15 μl of lipofectamine). The BAL cell differential (FIG. 7A) and the levels of cytokines in the BALs (FIG. 7B) were determined two days after the cell transfer. The cytokine measurement was performed by an ELISA. Statistical analysis was performed as described in the legend to FIG. 6.

DETAILED DESCRIPTION OF THE PREFERRED EMBODIMENTS

It is a discovery of the present inventors that local administration of a gene construct which causes expression of IFN-γ reverses allergic inflammation and hyperreactivity. In a preferred embodiment of the invention the gene construct encodes IFN-γ, and the local administration is via nebulization/aspiration to lung mucosa. When other atopic diseases are similarly treated, therapeutic benefits are achieved which are superior to those provided by either local or systemic administration of IFN-γ protein. The gene therapy approach described herein provides several advantages in that a single administration of the transgene is sufficient to provide continuous local levels of cytokine which have therapeutic benefit, while limiting potential systemic side effects by being compartmentalized to the lung.

Local administration is achieved according to methods which are known in the art and which are selected as is appropriate for a particular target tissue or disease. For example, for allergic rhinitis the gene construct can be administered intranasally. For atopic dermatitis (eczema) the gene construct can be administered intradermally. For treatment of allergic asthma, administration is to the bronchia or lungs. Other allergic diseases can be similarly treated by selection of an appropriate means of delivery to the affected organs.

Expression constructs for IFN-γ are any which are known in the art that will cause expression in mammalian cells. Suitable promoters and other regulatory sequences can be selected as is desirable for a particular application. The CMV (cytomegalovirus) promoter has been found to be suitable, but others can be used as well. A promoter which directs robust expression is desirable. Applicants have used a construct which encodes the signal sequence of IFN-γ. Such a sequence may not be required, however.

It has been found that liposomes greatly enhance the rate of uptake of the cytokine-encoding gene construct. Other agents which facilitate DNA uptake may also be used. For example, it may be desirable to package the gene construct in viruses, such as adenovirus, for administration to a particular target population of cells. Such packaging, and judicious choice of virus, will enhance the rate of DNA uptake by the target cells. Viruses having a tropism for a particular cell type are desirable, in this context.

The following examples are provided for exemplification purposes only and are not intended to limit the scope of the invention which has been described in broad terms above.

EXAMPLES

Example 1

Production of IFN-γ Gene Expression Construct

Figure 1:
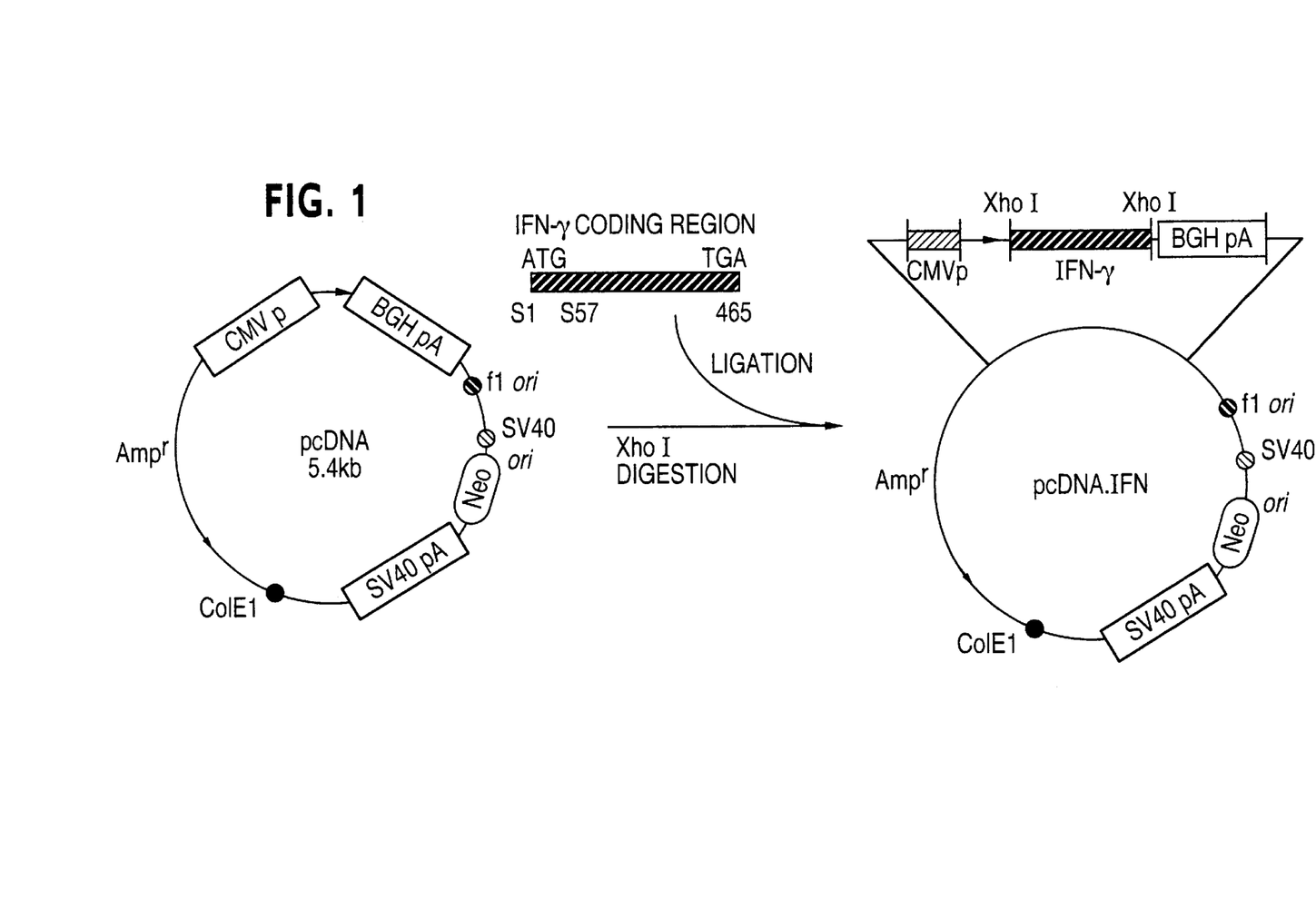

To generate a murine IFN-γ gene expression construct, the IFN-γ coding region gene was amplified from concanavalin-A stimulated mouse spleen cells by PCR. The PCR products were cloned in a TA vector and an Xho I fragment of the insert was her cloned into the polylinker site of an expression vector, pcDNA3. This shuttle vector contained a CMV promoter, bovine growth hormone poly A tail, and a neo gene to allow in vitro selection (FIG. 1).

Figure 2:
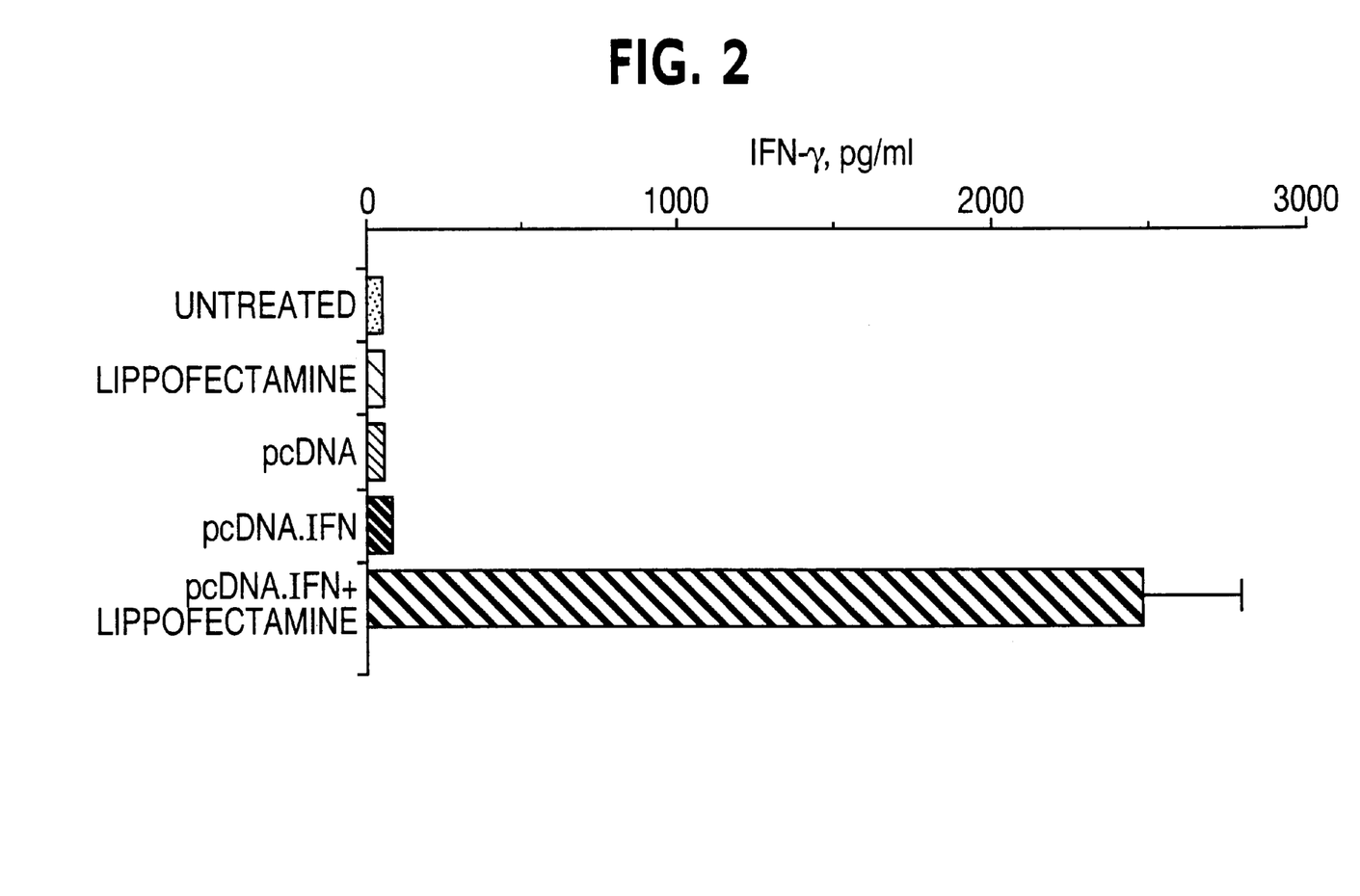

Confirmation of the effectiveness of the construct was initially obtained in vitro in the human epithelial cell line, BEAS-2B. Delivery of the IFN-γ transgene to epithelial cells in the log phase of growth in a plasmid/LipofectAmine complex resulted in production of significant amounts of murine IFN-γ as detected by ELISA (FIG. 2).

Example 2

Detection of Transduced Genes in Vivo

Figure 3A:
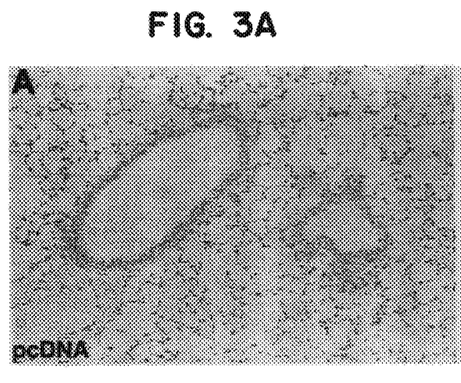
Figure 3B:
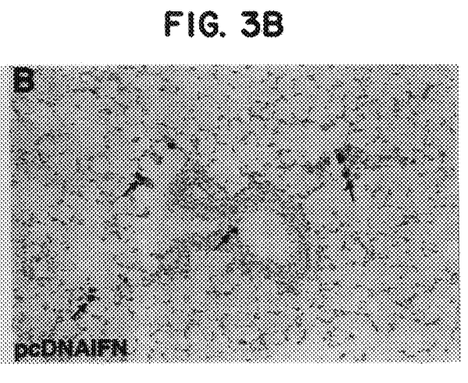

Following administration of the plasmid pcDNAIFN-liposome mix through aspiration, the lungs of mice were collected at 12- and 24-hr time points, fixed in 4% paraformaldehyde and the expression of transduced IFN-γ genes was analyzed by in situ hybridization. The lung sections were pretreated with 10 μg/ml proteinase K at 37° C. for 7 min. Hybridization was performed by using sense and antisense-IFN-γ riboprobes labeled with digoxigenin. Hybridization of pcDNA (vector) and pcDNAIFN-treated lung tissues were performed in parallel overnight, followed by the treatment with anti-digoxigenin antibody conjugate for one hr. at room temperature. Following extensive washings, the slides were treated with color substrate containing NBT and X-phosphate. The slides were then counter-stained with Nuclear Fast Red, and mounted. Representative results of pcDNA- (mock; FIG. 3A) and pcDNAIFN-treated (FIG. 3B) lungs (distal bronchiols) at 24-hr time point are shown. Results showed a dominant expression (indicated by the arrows) of transduced IFN-γ in the epithelium with few positive-stained pneumocytes in the lungs of mice treated with pcDNA IFN (10 μg/mouse).

Example 3

Expression of Transduced IFN-γ Assayed by ELISA of BAL Fluids

Figure 4:
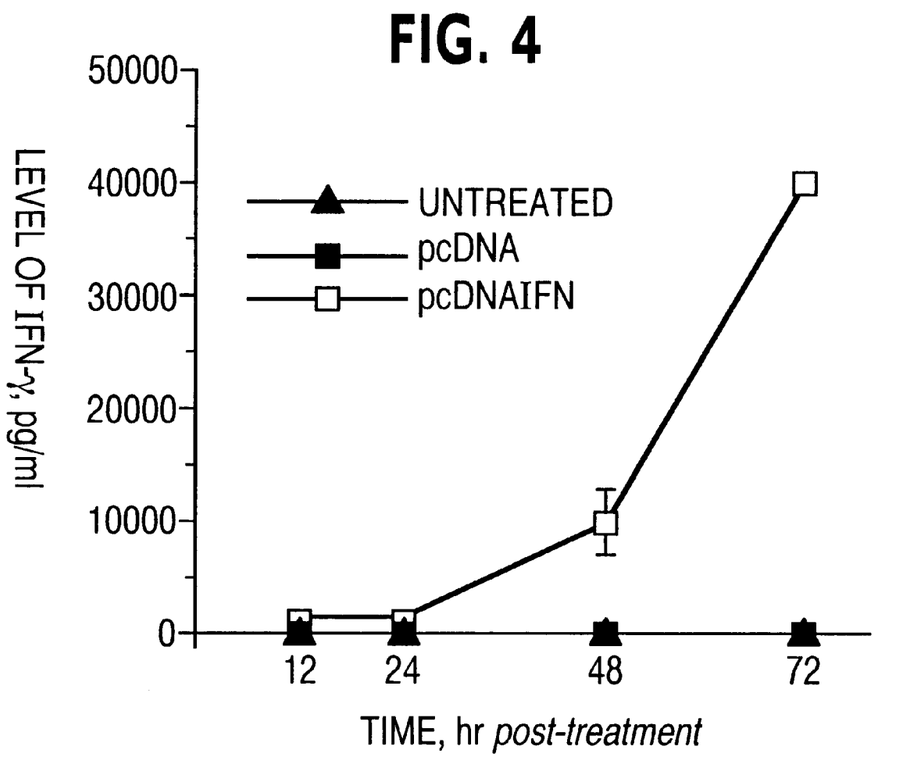
FIG. 4. Levels of IFN-γ in the BALs of mice either untreated or treated with pcDNA (mock) or pcDNAIFN determined by ELISA. The supernatants from BAL (bronchoalveolar lavage) fluids collected at different time points (as indicated), or a twelve 1:2 serial dilution of rIFN-γ standard was run in parallel. The levels of IFN-γ in either untreated or mock-treated samples were below detection limit (10 pg/ml).

We analyzed the tissue expression following administration of the plasmid (pcDNAIFN; 5 or 10 μg/mouse)-liposome mix through aspiration. The expression of the transduced IFN-γ was analyzed by ELISA assays of the BAL fluids collected at various time points (12, 24, 48, and 72 hr) from three different groups of mice. Mice (4 mice /group) received either no treatment or pcDNA (mock; 10 μg/mouse) or pcDNAIFN (10 μg/mouse). Results (FIG. 4) showed that while the BALs of untreated or mocked-treated mice have no detectable IFN-γ (<10 pg/ml; detection limit), a kinetic increase of IFN-γ level is observed over four time points in mice treated with pcDNAIFN (FIG. 4). Even at 12-hr time point a significant level (1250±55 pg/ml) of IFN-γ was detected.

Example 4

Confirmation of in Vivo Transfer of IFN-γ and its Localized Expression

The presence of pcDNAIFN-γ constructs and the expression of IFN-γ transcripts in antigen-treated and IFN-γ gene-transduced mice was confirmed by PCR. To analyze the expression of the IFN-γ gene in mice, an aliquot of total RNA (1 μg) was reverse-transcribed to cDNA in the presence of avian myeloblastosis virus reverse transcriptase (2.5 U/ml), 1 mM each of the dNTPs (dATP, dCTP, dGTP, and dTTP), RNase inhibitor (1 U/ml), oligo(dT)16 (2.5 μM, 10x PCR buffer (500 mM KCl, 100 mM Tris-HCl; pH 8.3) and MgCl₂ (5 mM) to a total volume of 20 μl. The RT-mix was incubated at 42° C. for 20 min for reverse transcription, followed by 99° C. for 5 min to inactivate the reverse transcriptase, followed by PCR in the presence of a "master mix" containing PCR buffer, MgC₂ (final concentration, 1.5 mM), dNTPs (final concentration, 0.2 mM of each), Ampli-Taq polymerase (Perkin-Elmer-Cetus; 1 U/50 μl reaction) and paired primers for a "housekeeping" gene, HPRT, and IFN-γ (0.5, μM of each primer) to a total volume of 50 μl. PCR was carried out under the following conditions: denaturation at 95° C. for 1 min, annealing at 55° C. for 1 min, and extension at 72° C. for 1 min. The numbers of PCR cycles were as follows: for HPRT, 27 cycles, and for IFN-γ, 32 cycles. Final extension was at 72° C. for 10 min. For amplification of IFN-γ and neo phosphotransferase genes, 1 μg of DNA from each sample was subjected to PCR using the paired primers for IFN-γ and neo genes. PCR was carried out under the following conditions: denaturation at 95° C. for 45 sec, annealing at 60° C. for 45 sec, and extension at 72° C. for 1.5 min for 30 cycles. The reaction product was visualized on 1.5% agarose (consisting of 0.5 % Nusieve GTG, FMC, and 1% agarose, Sigma) electrophoresis in 1x TBE buffer containing 0.5 μg/ml ethidium bromide. The RT-PCR assay results in a fragment size of 468 bp for IFN-γ, 164 bp for HPRT, and 800 bp for neo genes. The primers used for the PCR were as follows: IFN-γ 5' primer, 5'-ATGAACGCTACACACTGCATCT-3' (SEQ ID No:5); 3' primer, 5'TCAGCAGCGACTCCTTTTCCGCTT-3'(SEQ ID No:1); HPRT 5' primer, 5'-GTTGGATACAGGCCAGACTTTGTTG-3' (SEQ ID No:2); 3' primer, 5'-GATTCAACTTGCGCTCATCTTAGGC-3' (SEQ ID No:3); neo 5' primer, 5'-ATGATTGAACAAGATGGATTGCACG-3' (SEQ ID No:5); 3' primer, 5'-TCAGAAGAACTCGTCAAGAAGGCGA-3' (SEQ ID No:4).

When PCR was conducted at subsaturating cycles of amplification, mice receiving 5 μg of pcDNAIFN-γ demonstrated significant induction of IFN-γ transcripts, while control mice showed no amplified products for IFN-γ. The expression of IFN-γ was not detectable in either spleens or livers of pcDNAIFN-transduced mice. Furthermore, the pcDNAIFN-γ gene construct was only localized to the lungs, as it was not present in either the spleens or livers of IFN-γ transduced mice. These results demonstrate that delivery of genes in plasmid/lipofectAmine complexes provides an effective means of increasing local lung levels of IFN-γ.

Example 5

Figure 5A:
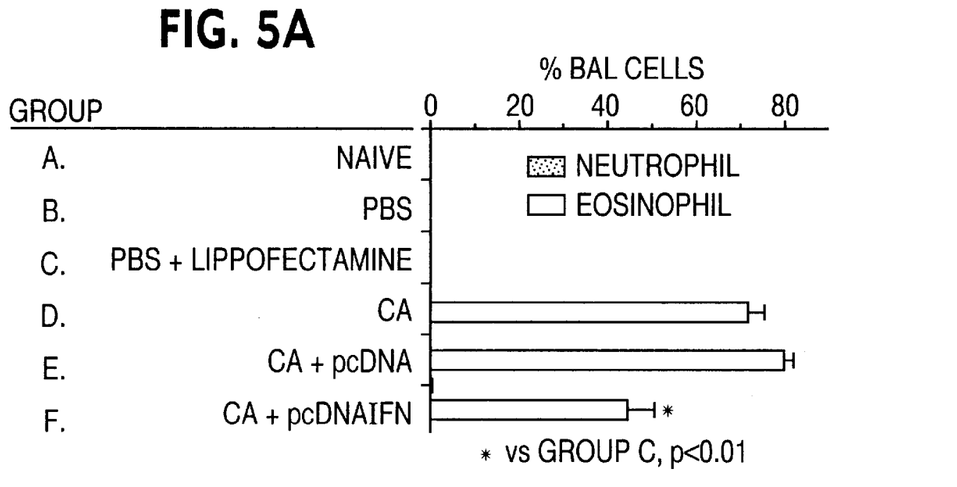
Figure 5B:
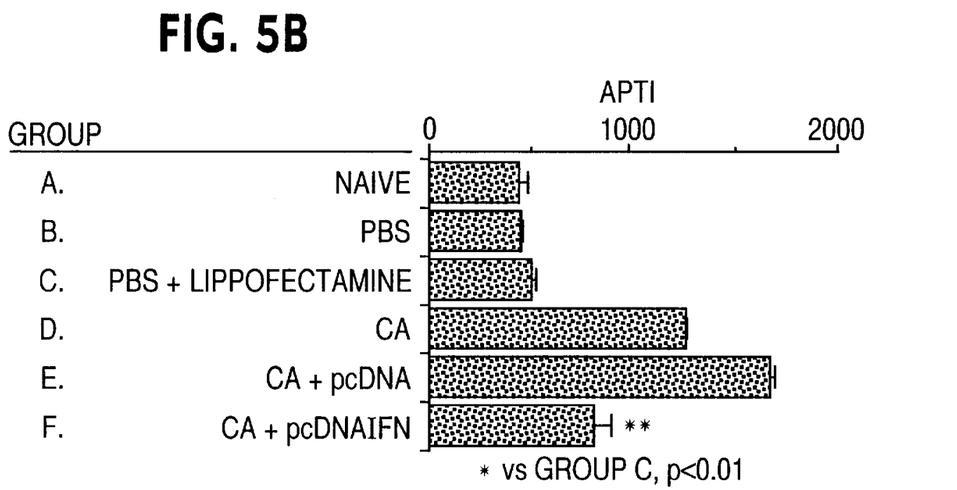
Figure 5C:
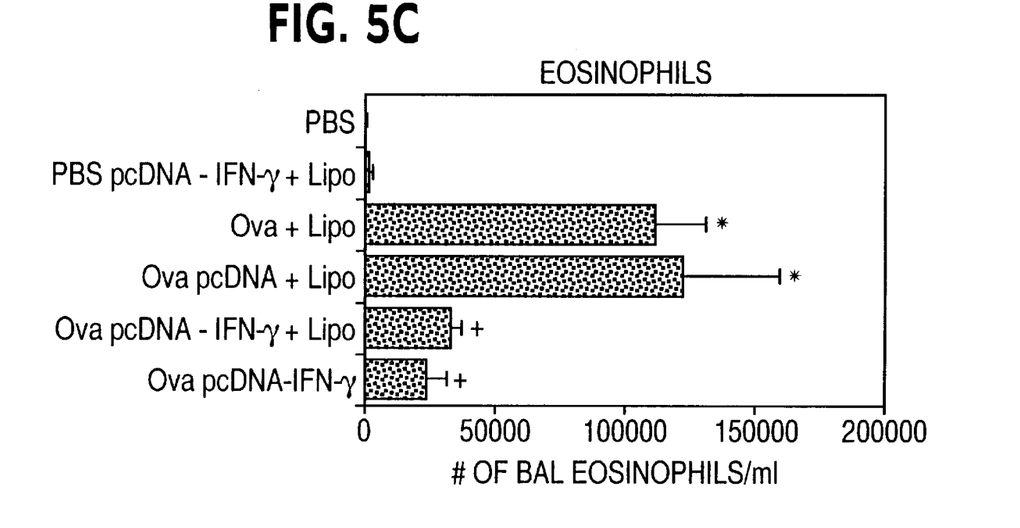
Figure 5D:
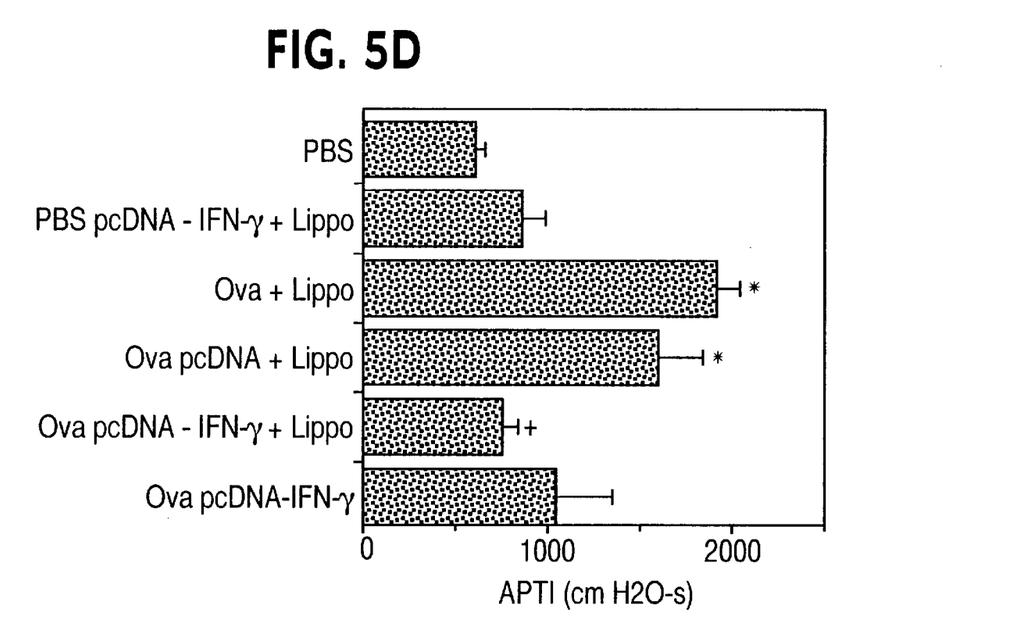

Evaluation of Efficacy of in Vivo Gene Transfer in Modulating Allergic Responses To evaluate the in vivo efficacy of cytokine gene transfer in modulating allergic responses, ovalbumin-immunized A/J mice (10 μg in 200 μl volume, i.p.) were administered either 50 μl of pcDNA (5 μg vector alone) or pcDNAIFN-γ in a complex with LipofectAmine (15 μl) by aspiration four days prior to five daily aerosol challenges with ovalbumin. Twenty four hours after the last inhalational challenge, airway reactivity to i.v. acetylcholine was examined. OVA-challenged A/j mice and ARK mice which received 5 μg of pcDNAIFN displayed a significant decrease in the number and percentage of eosinophils in the bronchoalveolar lavages (BAL) as shown in FIGS. 5A and 5C. Allergen treatment of A/J and AKR mice (sensitization and challenge with conalbumin) also induced marked increases in airway reactivity compared with PBS-sensitized and challenged controls (FIGS. 5B and 5D). Administration of the mock plasmid had no significant effect on airway responses of antigen-treated mice. Strickingly, IFN-γ transgene administration to antigen-treated mice completely ablated the development of airway hyperresponsiveness. Delivery of the pcDNAIFN-γ alone resulted in significant suppression of airway hyperresponsiveness, however, the use of liposomes greatly increased the efficacy of this suppression. These data are evidence that mucosal gene transfer can inhibit allergen-induced airway hyperreactivity.

Airway reactivity is estimated as the time integrated change in peak airway pressure, referred to as the airway pressure time index (APTI, cm H20-sec). Mice were anesthetized and instrumented as previously described (9). Mice were anesthetized with 60 mg/kg of sodium phenobarbital and a 20 gauge stainless steel cannula was ligated into place. Mice were ventilated with a constant tidal volume of air (0.2 ml per breath) at 120 breaths/min. A mixture of ketamine (50 mg/ml) and decamethonium bromide (25 mg/ml) were injected into the vena cava (1 μl/gm body weight) to provide further anesthesia and eliminate skeletal muscle movement. Airway pressure was measured from a port of the tracheal catheter. A stable recording of airway pressure is established for a period of 3 minutes, after which acetylcholine (50 μg/ml) is injected i.v. (25 μg/kg) at a constant rate by a pneumatic injector within 1 second, and the recording is continued for 5 minutes.

Example 6

Figure 6A:
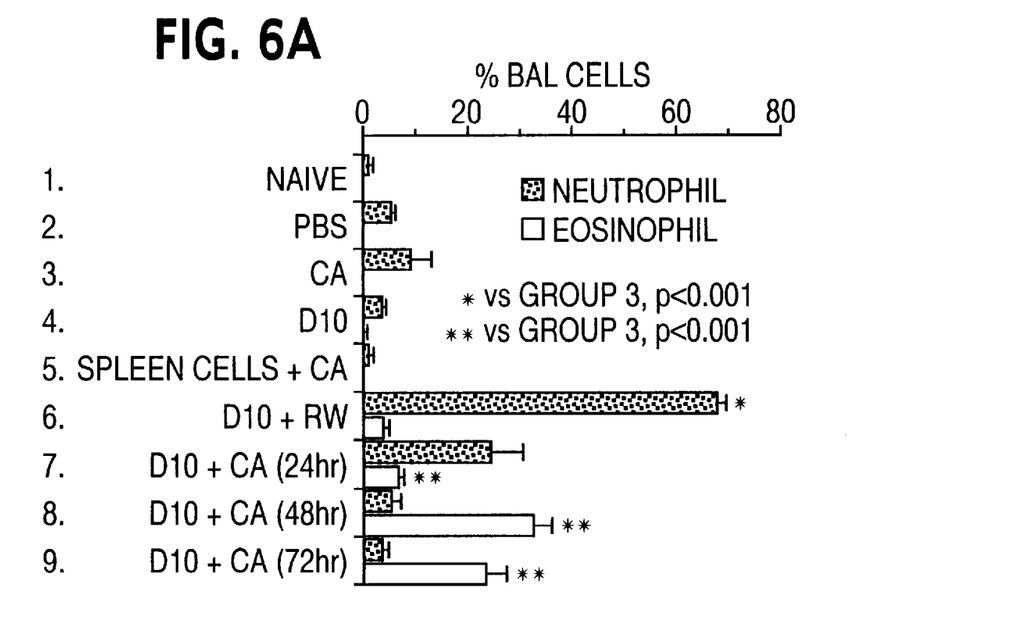
Figure 6B:
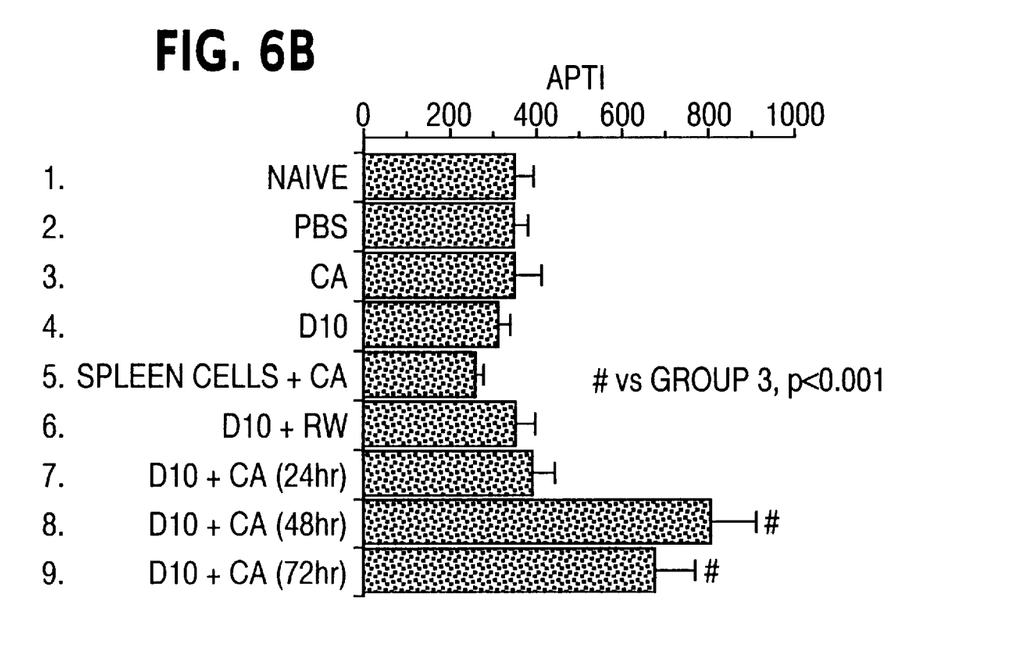

In Vivo Efficacy of Mucosal IFN-γ Gene Transfer in Adoptively Transferred Allergically Responsive Mice To provide direct evidence for the role of $T_{H2}$ cells in the pathogenesis of allergic pulmonary response, naive male AKR mice (6 weeks old; 8 mice per experimental group) were adoptively transferred intratracheally with a $T_{H2}$ clone, D10 (ref. 7; 5×10⁶ cells/mouse) mixed with or without Ag (CA; 50 µg/mouse) or a control Ag (RW; 50 µg/mouse). Twenty-four, 48-, and 72-hr after cell transfer, airway reactivity to i.v. acetylcholine was examined and the BAL differential cell count was made. Results (FIGS. 6A and 6B) show that while mice receiving Ag or D10 cells alone (groups 3 and 4, respectively) show similar levels of BAL eosinophils and airway responsiveness when compared to sham-treated mice (group 2), there is a significant increase of BAL eosinophils in Ag-challenged mice 24 hr (peaks at 48 hr) after D10 cell transfer (groups 7, 8, and 9), but not in mice transferred with autologous spleen cells (group 5). A significant increase of airway responsiveness was observed in Ag-challenged, D10-cell transferred mice at 48- and 72-hr after cell transfer. Of significance is the finding that the increase in the level of BAL eosinophils and airway reactivity is Ag-specific, since mice which received D10 cells and an irrelevant Ag (RW; group 6) show no signs of eosinophilic inflammation and airway hyperreactivity. In contrast, a predominant neutrophil influx was observed.

Figure 7A:
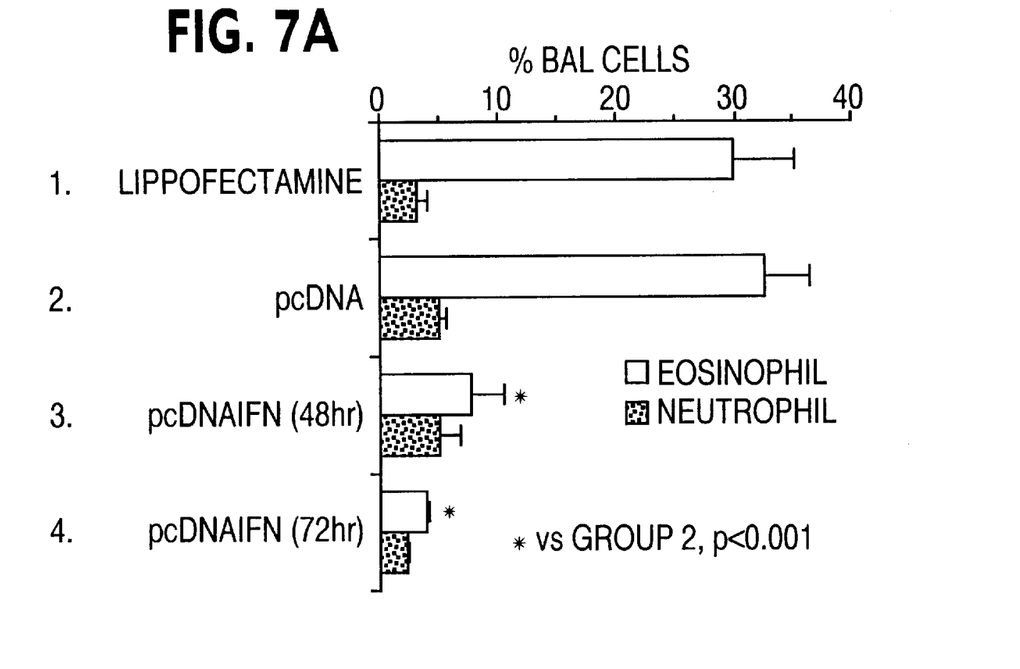
Figure 7B:
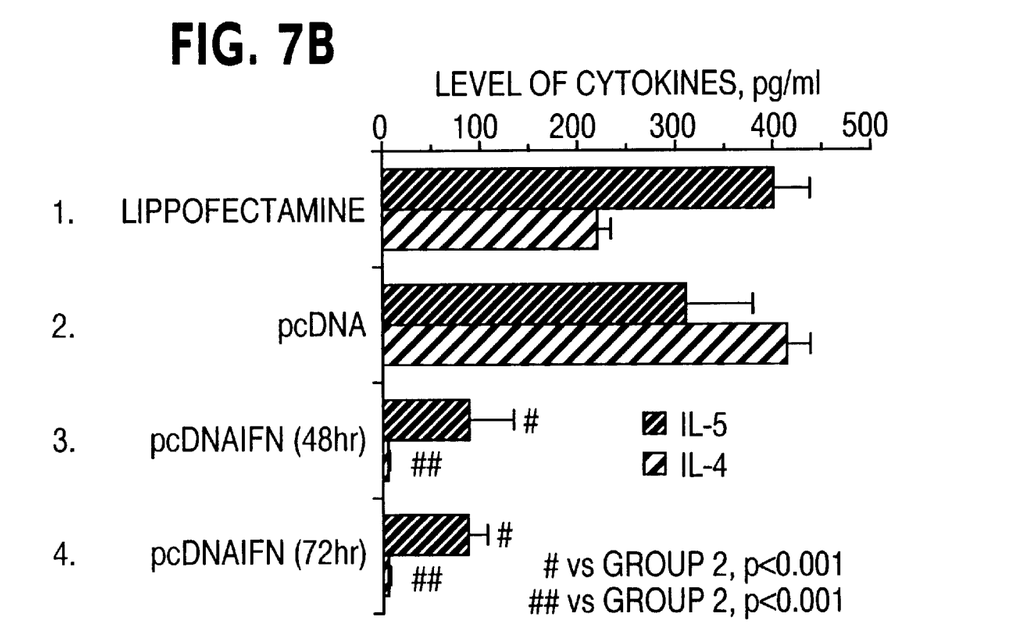

Naive male AKR mice (6 weeks old; 4 mice per group) were used following the same protocol as described above. Forty-eight or 72-hr prior to the cell transfer, mice aspirated 50 µl of the following: PBS alone, lipofectamine alone (15 µl lipofectamine in a total volume of 50 µl PBS); pcDNA+ lipofectaimne (5 µg plasmid+15 µl of lipofectamine); or pcDNAIFN+lipofectamine (5 µg plasmid+15 µl of lipofectamine). The BAL cell differential (FIG. 7A) and the levels of cytokines in the BALs (FIG. 7B) were determined two days after the cell transfer. The cytokine measurement was performed by an ELISA. ELISA plates were coated with 2 µl/ml of Rat anti-mouse IL-4, or IL-5, or IFN-γ diluted in NaHCO₃ buffer, pH 8.2. After overnight incubation at 4° C., plates were washed 2× and blocked with 10% FBS-PBS for 2 h at RT. The supernatants from BAL fluids, or 1:2 serial dilutions of cytokine standards were added to the plates and incubated overnight at 4° C., followed by the addition of biotinylated rat anti-mouse IL-4, or IL-5, or IFN-γ, and incubated for 45 min at RT. After washings, avidin peroxidase was added and incubated 30 min at RT, followed by the addition of color substrate, ABTS and developed. Plates were read at 410 nm in a microplate autoreader. Statistical analysis was performed the same as described in FIG. 6.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

REFERENCES

1. Antoon et al., J. Allergy and Clin. Immunol., 96, 104 (1995).
2. Boguniewicz et al., J. Alergy and Clin. Immunol., 95, 133 (1995).
3. Campbell, H. D., W. O. Tucker, Y. Hort, M. E. Martinson, G. Mayo, E. J. Clutteibuck, C. J. Sanderson, and I. G. Young. Proc. Natl. Acad. Sci. USA 84, 6629–6633 (1987).
4. Corrigan, C. J. Current Opinion in Biology 4, 798–804 (1992).
5. De Vries et al., Current Opinion in Immunology, 3, 851 (1991).
6. Foster, P. S., S. P. Hogan, A. J. Ramsay, K. I. Matthaei, and I.G. Young. J. Exp. Med. 183, 195–201 (1996).
7. Gajewski, T. F., and Fitch, F. W. J. Immunol. 140:4245–52 (1988).
8. Gavett et al., Am. J. Respir. Cell Mol Biol., 10, 587 (1994).
9. Gavett, D. O'Hearn, X.-M. Li, S. K. Huang, F. Finkelman, M. Wills-Karp, J. Exp. Med., 182, 1527 (1995).
10. Howarth et al, J. Respir. Crit. Care Med., 150, 518 (1994).
11. Huang et al., J. Immunol., 155, 2688 (1995).
12. Iwama, T., H. Nagai, N. Tsuruoka, and A. Koda. Clin. Exp. Allergy 23, 32–38 (1993).
13. Johnston, S. T. Holgate, Current Opinion in Immunology, 2, 513 (1990). 14. Kaye et a., J. Exp. Med., 158, 836 (1983).
15. Krishnaswamy et al., Amer. J. of Resp. Cell and Mol. Biol., 9, 279 (1993).
16. Lack et al., J. Immunol., 152, 2546 (1994).
17. Lopez, A. F., C. J. Sanderson, J. R. Gamble, H. R. Campbell, I. G. Young, and Vadas, M. A. J. Exp. Med. 167, 219–224 (1988).
18. Mauser, P. S., A. Pitman, A. Witt, X. Fernandez, J. Zurcher, T. Kung, H. Jones, A. S. Watnick, R. W. Gean, W. Kreutner, and G. K. Adams. Am. Rev. Respir. Dis. 148, 1623–1627 (1993).
19. Mosmann, R. L. Coffinan, Ann. Rev. Immunol., 7, 145 (1989).
20. Nakajima, H., A. Nakao, Y. Watanabe, S. Yoshida, and I. Iwamoto. J. Immunol. 153, 1264–1270 (1994).
21. Ohnishi et aL, Am. Rev. Respir. Dis., 147, 901 (1993).
22. Pene, J. F., Rousset, F. Briere, I. Chretien, J. Y. Bonnefoy, H. Spits, T. Yokota, N. Arai, K. I. Arai, J. Banchereau, and J. E. De Vries. Proc. Natl. Acad Sci. USA 85, 6880 (1988).
23. Renz et al., J. Immunol., 151, 1907, (1993).
24. Robinson, D. S., et al. N. Engl. J. Med. 326, 298–304 (1992).
25. Robinson et al, J. Allergy Clin. Immunol., 92, 313 (1993).
26. Romagnani, Immunol. Today, 11, 316 (1990).
27. Swain et al., Immunol. Rev., 123, 115 (1991)
28. Walker, C., et al. Am. Rev. Respir. Dis. 146, 109–115 (1992).
29. Watanabe et al., J. Clin. Invest., 96, 1303 (1995).
30. Yamaguchi, Y., T. Suda, S. Ohta, K. Tominaga, Y. Miura, and T. Kasahara. Blood, 78, 2542–2547 (1991).
31. Yssel et al., Res. Immunol., 144, 610 (1993).

What is claimed is:

1. A method for treating a disease associated with allergic airway reactivity, comprising the step of:

locally administering to a lung cell within a patient susceptible to allergic airway reactivity an effective amount of a preparation comprising liposomes and a plasmid DNA expression construct, wherein the plasmid DNA expression construct comprises a human IFN-γ coding sequence operably linked to a promoter, whereby an effective amount of IFN-γ is expressed within the lung cell, and whereby airway reactivity in the lung is reduced.

2. The method of claim 1 wherein the disease associated with allergic airway reactivity is asthma.

3. The method of claim 2 wherein the mode of local administration is by inhalation to the lung mucosa of the patient.

4. The method of claim 2 wherein pulmonary function in the patent is improved by the local administration.

5. The method of claim 1 wherein the DNA expression construct comprises a CMV promoter controlling the expression of human IFNγ.

6. The method of claim 1 wherein the DNA expression construct comprises a bovine growth hormone poly-A tail 3' to the human IFNγ coding sequence.

7. The method of claim 1 wherein the DNA expression construct further comprises a human IFN-γsignal sequence.

8. The method of claim 1 wherein the DNA expression construct comprises an adenovirus origin of replication.

* * * * *

UNITED STATES PATENT AND TRADEMARK OFFICE
CERTIFICATE OF CORRECTION

PATENT NO. : 6,121,247
DATED : September 19, 2000
INVENTOR(S) : Shau-Ku Huang, et al Page 1 of 1

It is certified that error appears in the above-identified patent and that said Letters Patent is hereby corrected as shown below:

On the cover page, left column, between items [22] and [51], the following has been inserted:

--Related U.S. Application Data

Provisional Application Serial No. 60/014,398, March 29, 1996.--.

Signed and Sealed this

Twelfth Day of June, 2001

*Attest:*

*Attesting Officer*

NICHOLAS P. GODICI
*Acting Director of the United States Patent and Trademark Office*